(12) United States Patent
Klimpel et al.

(10) Patent No.: US 6,592,872 B1
(45) Date of Patent: Jul. 15, 2003

(54) TARGETING ANTIGENS TO THE MHC CLASS I PROCESSING PATHWAY WITH AN ANTHRAX TOXIN FUSION PROTEIN

(75) Inventors: Kurt Klimpel, San Diego, CA (US); Theresa J. Goletz, Kensington, MD (US); Naveen Arora, Delhi (IN); Stephen H. Leppla, Bethesda, MD (US); Jay A. Berzofsky, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/937,276

(22) Filed: Sep. 15, 1997

Related U.S. Application Data

(60) Provisional application No. 60/025,270, filed on Sep. 17, 1996.

(51) Int. Cl.[7] .................. A61K 39/07; A61K 39/02; C07K 14/32; C07K 19/00

(52) U.S. Cl. ................ 424/197.11; 424/183.1; 424/192.1; 424/236.1; 424/246.1; 424/184.1; 424/193.1; 424/195.11; 514/2; 514/885; 530/350; 530/323; 530/403; 530/402; 530/806; 530/825

(58) Field of Search ................ 530/350, 323, 530/403, 402, 806, 825; 536/23.4, 23.7; 424/183.1, 192.1, 197.1, 236.1, 246.1, 184.1, 193.1, 195.11; 514/2, 885

(56) References Cited

U.S. PATENT DOCUMENTS 5,591,631 A   1/1997   Leppla

FOREIGN PATENT DOCUMENTS

| EP | 0532090 A2 * | 3/1993 |
|---|---|---|
| WO | WO 92/19720 | 11/1992 |
| WO | WO 94/18332 | 8/1994 |
| WO | WO 97/23236 | 7/1997 |

OTHER PUBLICATIONS

Milne et al. Molecular Immunol. 15:661, 1995.*
Radha, C., et al. (1996) "Thermostabilization of protective antigen—the binding component of anthrax lethal toxin", *Journal of Biotechnology* 50:235–242.
Ballard, Jimmy D., et al. (1996) "Anthrax toxin–mediated delivery of a cytotoxic T–cell epitope in vivo", *Proc. Natl. Acad. Sci. USA*, 93:12531–12534.
Sirard, Jean–Claude, et al. (1997) "A Recombinant *Bacillus anthracis* Strain Producing the *Clostridium perfringens* Ib Component Induces Protection against Iota Toxins", *Infection and Immunity*, 65(6): 2029–2033.

Goletz, T.J., et al. (1997) "Delivery of Antigens to the MHC Class I Pathway Using Bacterial Toxins", *Human Immunology* 54:129–136.
Carbonetti, N., et al. (1995) "Use of Pertussis Toxin Vaccine Molecule PT9K/129G to Deliver Peptide Epitopes for Stimulation of a Cytotoxic T Lymphocyte Response", *Abstr. Annu. Meeting Amer. Soc. Microbiology* 95:295, No. E–86.
Carbonetti, N., et al. (1996) "Development of Pertussis and Cholera Toxins as Cytotoxic T Lymphocyte Vaccine Vector Molecules", *Abstr. Annu. Meeting Amer. Soc. Microbiology* 96, No. E–59.
Ballard, Jimmy D., et al. (1997) "Anthrax Toxin–Mediated Delivery of Listeria Specific CTL Epitopes in vivo", *Abstr. Annu. Meeting Amer. Soc. Microbiology* 97, No. B–99.
Doling, A.M., et al. (1997) "Anthrax Toxin as a Delivery System for Viral and Bacterial Cytotoxic T–Cell Epitopes", *Abstr. Annu. Meeting Amer. Soc. Microbiology* 97, No. B–101.
Donnelly, John, J., et al. (1993) "Targeted delivery of peptide epitopes to class I major histocompatibility molecules by a modified Pseudomonas exotoxin", *Proc. Natl. Acad. Sci. USA*, 90:3530–3534.
Fayolle, Catherine, et al. (1996) "In Vivo Induction of CTL Responses by Recombinant Adenylate Cyclase of *Bordetella pertussis* carrying Viral CD8[+] T Cell Epitopes", *Journal of Immunology* 4697–4706.
Madshus, Inger Helene, et al. (1991) "Entry of Diphtheria Toxin–Protein A Chimeras into Cells", *The Journal of Biological Chemistry*, 266(26):17446–17453.
Madshus, Inger Helene, et al. (1992) "Membrane Translocation of Diphtheria Toxin Carrying Passenger Protein Domains", *Infection and Immunity*, 60(8):3296–3302.
Perelle, Sylvie, et al. (1993) "Characterization of *Clostridium perfringens* Iota–Toxin Genes and Expression in *Escherichia coli*", *Infection and Immunity* 61(12):5147–5156.
Sebo, Peter, et al. (1995) "Cell–Invasive Activity of Epitope–Tagged Adenylate Cyclase of *Bordetella pertussis* Allows In Vitro Presentation of a Foreign Epitope to CD8[+] Cytotoxic T Cells", *Infection and Immunity*, 63(10):3851–3857.

(List continued on next page.)

Primary Examiner—Ronald B. Schwadron
(74) Attorney, Agent, or Firm—Townsend and Townsend and Crew LLP

(57) ABSTRACT

The present invention provides a vaccine for inducing an immune response in mammal to a specific antigen, where the vaccine comprises a unit dose of a binary, cytotoxic T lymphocyte vaccine comprising an anthrax protective antigen and a full length protein antigen bound to a nontoxic anthrax protective antigen binding protein comprising at least about the first 250 amino acid residues of the lethal factor of *Bacillus anthracis* and less than all of the amino acid residues of the lethal factor. The present invention also provides a method of immunizing a mammal against an antigen using the vaccine, and a method of inducing antigen–presenting mammalian cells to present specific antigens via the MHC class I processing pathway.

10 Claims, No Drawings

OTHER PUBLICATIONS

Ulmer, Jeffrey B., et al. (1994) "Presentation of an exogenous antigen by major histocompatibility complex class I molecules", *Eur. J. Immunology*, 24:1590–1596.

Arora, Naveen, et al. (1994), "Cytotoxic Effects of a Chimeric Protein Consisting of Tetanus Toxin Light Chain and Anthrax Toxin Lethal Factor in Non–neuronal Cells", *The Journal of Biological Chemistry*, 269 (42):26165–26171.

Arora, Naveen, et al. (1994) "Fusions of Anthrax Toxin Lethal Factor with Shiga Toxin and Diphtheria Toxin Enzymatic Domains are Toxic to Mammalian Cells", *Infection and Immunity*, 62(11):4955–4961.

Arora, Naveen, et al. (1993) "Residues 1–254 of Anthrax Toxin Lethal Factor Are Sufficient to Cause Cellular Uptake of Fused Polypeptides", *The Journal of Biological Chemistry* 268(5):3334–3341.

Singh, Yogendra, et al. (1991) "The Carboxyl–terminal End of Protective Antigen is Required for Receptor Binding and Anthrax Toxin Activity", *The Journal of Biological Chemistry*, 266(23):15493–15497.

Arora, Naveen, et al. (1992) "Fusions of Anthrax Toxin Lethal Factor to the ADP–Ribosylation Domain of Pseudomonas Exotoxin A are Potent Cytotoxins which are Translocated to the Cytosol of Mammalian Cells", *The Journal of Biological Chemistry*, 267(22): 15542–15548.

\* cited by examiner

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..36
      (D) OTHER INFORMATION: /note= "primer 1"

(xi) SEQUENCE DESCRIPTION: SEQ ID NO: 1:

TCTAGATCTA GAAGCGGGCG GTCATGGTGA TGTAGG      36

(2) INFORMATION FOR SEQ ID NO: 2:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..37
      (D) OTHER INFORMATION: /note= "primer 2"

(xi) SEQUENCE DESCRIPTION: SEQ ID NO: 2:

GATCTTTAAG TTCACGCGTG GATAGATTTA TTTCTTG      37

(2) INFORMATION FOR SEQ ID NO: 3:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..32
      (D) OTHER INFORMATION: /note= "primer 3"

(xi) SEQUENCE DESCRIPTION: SEQ ID NO: 3:

GCAAGACGCG TCTGCAGATG AGAGTGAAGG AG      32

(2) INFORMATION FOR SEQ ID NO: 4:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: DNA (ix) FEATURE:

-continued

```
(A) NAME/KEY: -
(B) LOCATION: 1..38
(D) OTHER INFORMATION: /note= "primer 4"

(xi) SEQUENCE DESCRIPTION: SEQ ID NO: 4:

ATCCGCTCGA GTCTAGATTA TCTTTTTTCT CTCTGCAC                         38

(2) INFORMATION FOR SEQ ID NO: 5:

(i) SEQUENCE CHARACTERISTICS:
     (A) LENGTH: 10 amino acids
     (B) TYPE: amino acid
     (C) STRANDEDNESS: <Unknown>
     (D) TOPOLOGY: linear (ii) MOLECULE TYPE: peptide (xi) SEQUENCE DESCRIPTION: SEQ ID NO: 5:

Arg Gly Pro Gly Arg Ala Phe Val Thr Ile
1               5                   10
```

TARGETING ANTIGENS TO THE MHC CLASS I PROCESSING PATHWAY WITH AN ANTHRAX TOXIN FUSION PROTEIN

CROSS REFERENCE TO RELATED APPLICATIONS

This application claims the benefit of provisional application No. 60/025,270, filed Sep. 17, 1996.

FEDERALLY SPONSORED RESEARCH OR DEVELOPMENT

Not applicable.

BACKGROUND OF THE INVENTION

The mammalian system reacts to invading pathogens by mounting two broad defenses: the cell-mediated response and the humoral response. Viral and other intracellular infections are controlled primarily by the cell-mediated immune system. This control is achieved through recognition of foreign antigen displayed on the cell surface of an infected cell. The present invention describes a vaccine that stimulates the cell-mediated immune system and a method for immunizing mammals. The present invention also describes a method for inducing antigen-presenting cells to present specific antigens using the MHC class I processing pathway.

The cell-mediated immune system responds to endogenous antigen presented by the MHC class I processing pathway. Cells can process foreign proteins found in the cell cytosol and display relevant peptide epitopes using this processing pathway (Harding, in *Cellular Proteolytic Systems*, pp. 163–180 (1994); Carbone & Bevan, in *Fundamental Immunology*, pp. 541–567 (Paul, ed., 1989); Townsend & Bodmer, *Annu. Rev. Immunol.* 7: 601–624 (1989)). The MHC class I processing pathway involves digestion of the antigen by the proteasome complex and transport of the resulting peptides into the endoplasmic reticulum, where they bind to nascent MHC class I molecules (Germain & Margulies, *Annu. Rev. Immunol.* 11: 403–450 (1993)). Cytotoxic T lymphocytes (CTLs) specifically recognize the foreign antigen displayed by the MHC class I molecules and lyse the antigen-presenting cells. A population of memory T cells is also established that can react to presentation of the specific antigen. The cellular immune system is thus primed to swiftly respond to an intracellular infection by a pathogenic organism such as a virus.

The objective for a vaccine that stimulates the cell-mediated immune system is to deliver protein antigen to the cell cytosol for processing and subsequent presentation by MHC class I molecules. Several bacterial toxins including diphtheria toxin (DT), Pseudomonas exotoxin A (PE), pertussis toxin (PT), and the pertussis adenylate cyclase (CYA) have been used in attempts to deliver peptide epitopes to the cell cytosol as internal or amino-terminal fusions (Stenmark et al., *J. Cell Biol.* 113: 1025–1032 (1991); Donnelly et al., *Proc. Natl. Acad. Sci. U.S A.* 90: 3530–3534 (1993); Carbonetti et al., *Abstr. Annu. Meet. Am. Soc. Microbiol.* 95: 295 (1995); Sebo et al., *Infect. Immun.* 63: 3851–3857 (1995)). These systems are restricted in their use as potential vaccines because they do not provide access to the MHC I processing pathway for antigen presentation, but instead likely operate through an alternative, less efficient pathway (see Kovacsovics-Bankowski & Rock, *Science* 267: 243–246 (1995); Rock, *Immunology Today* 17: 131–137 (1996)).

Surprisingly, the present invention provides antigen access to the MHC class I processing pathway via the anthrax binary toxin system. The *Bacillus anthracis* binary toxin consists of two distinct proteins (Smith & Stoner, *Fed. Proc.* 2: 1554–1557 (1967); Leppla, in *Bacterial Toxins and Virulence Factors in Disease. Handbook of Natural Toxins*, vol 8, pp. 543–572 (Moss et al., eds., 1995)). Protective antigen (PA) combines with lethal factor (LF) to make "lethal toxin" or "anthrax" toxin. (Friedlander, *J. Biol. Chem.* 261: 7123–7126 (1986); Leppla, *Proc. Natl. Acad. Sci. U.S.A.* 79, 3162–3166 (1982). In addition to lethal toxin, PA combined with edema factor (EF) makes edema toxin (Friedlander, Leppla, supra).

In this system, PA (83 kDa) binds to a protein receptor on the surface of cells. PA is then cleaved by a cellular protease (furin) and a amino-terminal 20-kDa fragment is released, leaving a 63-kDa fragment, PA63, bound to the cell (Leppla et al., in *Molecular Mechanisms of Bacterial Virulence*, pp. 127–139 (Kado & Crosa, eds., 1994); Klimpel et al., *Proc. Natl. Acad. Sci. U.S.A.* 89: 10277–10281 (1992)); Novak et al., *J. Biol. Chem.* 267: 17186–17193 1992)). PA63 binds to LF and the binary anthrax toxin is then endocytosed and transported into the cell. PA facilitates the delivery of LF from the endosome to the cytosol of the cell (Milne et al., *J. Biol. Chem.* 269: 20607–20612 (1994); Milne et al., *Mol. Microbiol.* 15: 661–666 (1995)). LF fusion proteins are also translocated into the cytosol by PA.

Once in the cytosol, in contrast to other binary toxin systems, the anthrax toxin and LF fusion proteins are processed by the MHC class I processing pathway. Cells treated with anthrax toxin fusion proteins are recognized and lysed by antigen specific CTLs. Dependence on processing via the MHC class I pathway was demonstrated by treating antigen-presenting cells with lactacystin, which inhibits proteasome function required for MHC class I processing. Thus, the anthrax toxin system can be used to create vaccines that efficiently stimulate the cell-mediated immune system.

In addition, binary toxins that have similar functional qualities can be used for the present invention. For example, the iota toxin of *Clostridium perfringens* is a binary toxin homologous to the lethal toxin of *B. anthracis*. Protein Ib of *C. perfringens* binds to protein Ia to form the toxin, and protein Ib is involved in cell surface binding and internalization of the toxin (Perelle et al., *Infect. Immun.*, 61: 5147–5156 (1993)). The predicted amino acid sequence of Ib shows 33.9% identity with and 54.4% homology with PA (Perelle, supra).

One advantage of the anthrax system is its ability to accommodate large fusion proteins. Unlike the anthrax system, other bacterial toxin systems are limited in their capacity to deliver large protein antigen to the cell. While peptides are able to stimulate a cell-mediated immune response, whole protein antigens may be better suited for use in an effective vaccine, for two reasons. First, the epitope that is essential for protection in one genetic background may be irrelevant in another. Therefore, it is beneficial for a broadly applied T-cell vaccine to use the full length protein from which the various relevant epitopes are derived. Second, epitopes recognized by CTL are processed from the whole protein by specialized degradative machinery. In certain instances, the processing of the relevant epitopes is dependent on the flanking amino acid sequences (Del Val et al., *Cell* 66: 1145–1153 (1991)). Because it is currently not possible to accurately predict which epitopes are dependent on their context for proper processing, it is important to deliver the entire antigen to the cell cytosol for optimal processing and presentation. A final drawback to other bacterial toxin systems is that many individuals have already been immunized against the carrier toxin. However, anthrax toxin is not widely used for immunization.

With this invention, the efficient delivery of anthrax fusion proteins to the cytosol can be safely used as a method to intracellularly inoculate living cells with whole protein antigens. These antigens are then displayed by MHC I molecules. This system provides the basis for new, potent vaccines that target the cell-mediated immune system.

SUMMARY OF THE INVENTION

The present invention provides a vaccine for inducing an immune response in a mammal to a specific antigen, where the vaccine comprises a unit dose of a binary toxin protective antigen and the specific antigen, which is bound to a binary toxin protective antigen binding protein.

In one embodiment of the invention, the vaccine is comprised of an anthrax or iota protective antigen and the antigen bound to anthrax or iota protective antigen binding protein.

In yet another embodiment of the vaccine, the protective antigen is processed protective antigen.

The preferred embodiment of the vaccine is sterile and comprises physiologically compatible salts, which in another embodiment may be in an aqueous solution.

In one embodiment of the vaccine, the anthrax protective antigen binding protein is the lethal factor of *B. anthracis*.

In another embodiment of the vaccine, the anthrax protective antigen binding protein comprises at least about the first 250 amino acid residues of the lethal factor of *B. anthracis*, and less than all of the amino acid residues of the lethal factor.

In yet another embodiment of the vaccine, the molar ratio of protective antigen to antigen bound to protective antigen binding protein is greater than one.

The present invention also provides a method of immunizing a mammal against an antigen by administering a safe and effective amount of a vaccine comprising anthrax protective antigen and the antigen bound to anthrax protective antigen binding protein.

The present invention also provides additional embodiments of this method of immunizing with a vaccine as described above.

In one embodiment of this method, the vaccine is administered via parenteral injection, and in another embodiment of the method the vaccine is administered via subcutaneous injection.

In another embodiment of this method the vaccine is administered in a unit dose that is between 10–500 ng of antigen bound to protective antigen binding protein per kg of animal.

The present invention also provides a method of inducing antigen-presenting mammalian cells to present specific antigens on their cell membrane via the MHC class I processing pathway. This method comprises first selecting cells that can process and present specific antigens on their cell membranes via the MHC class I processing pathway. Second, this method comprises contacting the cells with an anthrax protective antigen and the antigen bound to protective antigen binding protein. Third, the method comprises permitting the cells to internalize, process, and present the antigen bound to protective antigen binding protein on its cell membrane, forming an antigen-presenting cell.

In one embodiment of this method, the antigen-presenting cells are further contacted with an effector lymphocyte cell that recognizes the antigen present on the cell membrane of the antigen-presenting cell.

In another embodiment of this method, the protective antigen is processed protective antigen.

In yet another embodiment of this method, the antigen bound to protective antigen binding protein comprises at least about the first 250 amino acids of lethal factor of *B. anthracis* and less than all amino acid residues of the lethal factor.

In a further embodiment of this method, the molar ratio of protective antigen to antigen bound to protective antigen binding protein is greater than one.

In yet a further embodiment of this method, the antigen presenting cell is a dendritic cell.

DEFINITIONS

Unless defined otherwise, all technical and scientific terms used herein have the meaning commonly understood by one of ordinary skill in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. For purposes of the present invention, the following terms are further defined.

A "vaccine" is an antigenic preparation, including, e.g., a protein, a peptide, or a polysaccharide, administered to stimulate the recipient's humoral and cellular immune systems to one or more of the antigens present in the vaccine preparation. "Vaccination" or "immunization" is the process of administering a vaccine and stimulating an immune response to an antigen.

An "immune response" refers to the activities of the immune system, including activation and proliferation of specific cytotoxic T-cells, after contact with an antigen.

An "antigen" is any agent, e.g., a protein, a peptide, or a polysaccharide, that elicits an immune response.

A "unit dose" is a defined and predetermined concentration or amount of the vaccine that is a safe and therapeutically effective amount, which produces the desired result, e.g., an immune response, in the recipient of the vaccine.

The anthrax "protective antigen" (PA) is an 83 kDa protein produced by *Bacillus anthracis*. PA is one of two protein components of the lethal or anthrax toxin produced by *B. anthracis*. The 83 kDa PA binds at its carboxyl-terminus to a cell surface receptor, where it is specifically cleaved by a protease, e.g., furin, clostripain, or trypsin. This enzymatic cleavage releases a 20 kDa amino-terminal PA fragment, while a 63 kDa carboxyl-terminal PA fragment remains bound to the cell surface receptor. The description of protective antigen includes binary toxin functional equivalents such as protein Ib of *C. perfringens*.

"Anthrax protective antigen binding protein" (APABP) refers to a protein that contains the PA binding site of LF. APABP may correspond to a polypeptide representing the PA binding site of LF, or any larger portion of LF that contains this site, including the entire LF protein. The APABP is bound to a second protein or antigen. The antigen may be bound either at the amino- or carboxyl-terminus of the APABP. The description of APABP also includes binary toxin functional equivalents such as protein Ia of *C. perfringens*.

An antigen is "bound" to an anthrax protective antigen binding protein (APAPB) when it is associated as a complex with the APABP in a manner that allows translocation of the bound APABP-antigen complex into the cytosol of the cell via the action of PA. Methods of binding antigen to APAPB include the formation of covalent bonds through chemical coupling or protein synthesis. Antigen bound to APAPB may be synthesized as a single polypeptide from nucleic acid sequence encoding a single contiguous fusion protein.

"Processed protective antigen" refers to a 63 kDa PA fragment that results from the enzymatic cleavage of the 83 kDa PA. Processed PA contains both a cell surface receptor binding site at its carboxyl-terminus and a lethal factor binding site at its new amino-terminus. Processed PA may be produced by enzymatic cleavage in vitro or in vivo, or as a recombinant protein. The description of processed PA also includes binary toxin functional equivalents such as processed protein Ib of *C. perngens*.

Anthrax "lethal factor" (LF) is a 90 kDa protein that is the second protein component, along with PA, of the *B. anthracis* lethal or anthrax toxin. LF contains a PA binding site. The description of LF includes binary toxin functional equivalents such as protein Ia of *C. perfringens*

"Physiologically compatible salts" are compositions of salts that are safe and effective means for delivery of a vaccine to a recipient.

"MHC class I molecules" are receptors that bind peptide antigen ligands.

The "MHC class I processing pathway" is an intracellular pathway that results in the binding of a peptide antigen ligand to an MHC class I molecule and the presentation of the antigen-MHC class I complex on the cell surface. First, cytoplasmic antigen is partially processed (through the action of proteasomes) and enters the ER as a complex with a transporter protein. In the ER, MHC class I molecules stably associate with the peptide antigen. The antigen-MHC class I complex then passes through the trans-Golgi network in a secretory vesicle to the cell surface. Functionally, processing of a peptide antigen through the MHC class I processing pathway can be identified with the use of lactacystin. Lactacystin is a specific proteasome inhibitor. Lactacystin inhibition of antigen presentation demonstrates that processing of the antigen is dependent on the function of the proteasome complex rather than an alternative processing pathway.

"Effector" lymphocytes "recognize" antigens associated with MHC class I molecules on the surface of an antigen presenting cell. Recognition is an antigen specific event that occurs via receptors on the cell surface of the effector lymphocyte, which can then perform a variety of activities due to stimulation with a specific antigen.

"Parenteral" administration of a vaccine includes, e.g., subcutaneous, intravenous, intramuscular, or intrasternal injection or infusion techniques.

"Antigen presenting cells" are cells, e.g., dendritic cells or macrophages, that process peptide antigens through the MHC class I processing pathway so that the antigen-MHC class I complex is displayed on their cell surface.

A "dendritic" cell is a motile, non-phagocytic adherent cell that acts as an efficient antigen-presenting cell and moves readily between the lymph nodes and other organs. Dendritic cells are further classified into subgroups, including, e.g., follicular dentritic cells, Lagerhans dendritic cells, and epidermal dendritic cells.

"Molar ratio" and mole ratio are used interchangeably and refer to a ratio of components as determined either by concentration (molar) or amount (moles).

A "binary toxin" is a bacterial toxin that is composed of two separate proteins that associate to form the toxin.

"Iota toxin" is a binary toxin produced by *C. perfingens*, composed of Ia and Ib.

"Anthrax toxin" is a binary toxin produced by *B. anthracis*, composed of LF and PA. Anthrax toxin may also refer to the binary edema toxin of *B. anthracis*, composed of LF and EF (edema factor).

DETAILED DESCRIPTION

1. Antigen Bound to Anthrax Protective Antigen Binding Protein a. Introduction

Anthrax protective antigen binding protein (APABP) is any protein that contains the PA binding domain of the anthrax lethal factor protein (LF), or a functional equivalent. The region of LF that contains the PA binding domain has been investigated by structure-function analysis. Deletion analysis of the LF portion of an LF fusion protein shows that the PA binding domain is at the amino-terminus of LF (Arora et al., *J. Biol. Chem.*, 268: 3334–3341 (1993)). In this experiment, a fusion protein containing full size LF fused to a second protein was biologically active, that is, it was internalized into the cell by PA (Arora, supra (1993)). A fusion protein that contained amino-terminal residues 1–254 of LF also produced a biologically active fusion protein (Arora, supra (1993)). However, a fusion protein that contained amino-terminal residues 1–198 of LF produced a biologically inactive fusion protein (Arora, supra (1993)).

Thus, amino-terminal residues 1–254 of LF are sufficient for PA binding activity. Amino acid residues 199–253 may not all be required for PA binding activity. One embodiment of APABP is amino acids 1–254 of LF. Any embodiment that contains at least about amino acids 1–254 of LF can be used for APABP, for example, native LF. Nontoxic embodiments of APABP are preferred.

The antigen may be bound to either the amino- or the carboxyl-terminus of the APABP. The position of antigen does not affect the PA binding activity of APABP. In one embodiment of antigen-APABP, as described in Example 1A, antigen is bound to the carboxyl-terminus of APABP.

The antigen portion of "antigen bound to APABP" (antigen-APABP) can be any protein useful as an antigen for a vaccine for mammals. Other suitable antigens include, for example, proteins from infectious organisms such as cytomegalovirus proteins; hepatitis C proteins; *Plasmodium malariae* proteins; *Schistosoma mansoni* proteins; and HIV proteins such as NEF, RT, TAT, REV, and gp41. In Example 1A, HIV envelope protein gp120 is one embodiment of such a suitable antigen. The use of gp120 as an antigen is demonstrated by cloning and expressing gp120 as antigen-APABP. In Example 1B herpes simplex virus protein NS-5b is similarly described.

b. Cloning and Expression of a Recombinant APABP-antigen

A recombinant nucleic acid that encodes two different proteins is prepared by first isolating the nucleic acids. The nucleic acids are then joined so that a single recombinant nucleic acid molecule is formed, for example, using restriction endonuclease sites at the ends of the molecule for directed ligation. The recombinant molecule encoding the fusion protein is then ligated into a vector suitable for expression of the protein. Methods for preparing a recombinant nucleic acid encoding a fusion protein are known by those skilled in the art (see Sambrook et al., *Molecular Cloning: A Laboratory Manual* (2d ed. 1989)).

One preferred method for obtaining specific nucleic acids encoding fusion proteins combines the use of synthetic oligonucleotide primers with polymerase extension on a mRNA or DNA template. This PCR method amplifies the desired nucleotide sequence (see also U.S. Pat. Nos. 4,683, 195 and 4,683,202). Restriction endonuclease sites can be incorporated into the primers. Genes amplified by PCR can be purified from agarose gels and ligated together. Alterations in the natural gene sequence can be introduced by techniques such as in vitro mutagenesis and PCR using primers that have been designed to incorporate appropriate mutations.

The gene encoding a fusion protein can be inserted into an "expression vector," "cloning vector," or "vector," terms which usually refer to plasmids or other nucleic acid molecules that are able to replicate in a chosen host cell. Expression vectors can replicate autonomously, or they can replicate by being inserted into the genome of the host cell. Often, it is desirable for a vector to be usable in more than one host cell, e.g., in *E. coli* for cloning and construction, and in a mammalian cell for expression. Additional elements of the vector can include, for example, selectable markers and enhancers. Selectable markers, e.g., tetracycline resistance or hygromycin resistance, permit detection and/or selection of those cells transformed with the desired DNA sequences (see, e.g., U.S. Pat. No. 4,704,362).

The particular vector used to transport the genetic information into the cell is also not particularly critical. Any of the conventional vectors used for expression of recombinant proteins in prokaryotic or eukaryotic cells can be used.

The expression vectors typically have a transcription unit or expression cassette that contains all the elements required for the expression of the DNA encoding a protein of the invention in the host cells. A typical expression cassette contains a promoter operably linked to the DNA sequence encoding the protein. The promoter is preferably positioned about the same distance from the heterologous transcription start site as it is from the transcription start site in its natural setting. As is known in the art, however, some variation in this distance can be accommodated without loss of promoter function.

In the expression cassette, the DNA sequence encoding the fusion protein can be linked to a cleavable signal peptide sequence to promote secretion of the encoded protein by the transformed cell. The expression cassette should also contain a transcription termination region downstream of the structural gene to provide for efficient termination. The termination region can be obtained from the same gene as the promoter sequence or can be obtained from a different gene.

For more efficient translation in mammalian cells of the mRNA encoded by the structural gene, polyadenylation sequences are also commonly added to the expression cassette. Termination and polyadenylation signals that are suitable for the present invention include those derived from SV40, or a partial genomic copy of a gene already resident on the expression vector.

In addition to the expression cassette, many expression vectors optimally include enhancer elements can stimulate transcription up to 1,000 fold from linked homologous or heterologous promoters. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long terminal repeat from various retroviruses such as murine leukemia virus, murine or Rous sarcoma virus, and HIV (see *Enhancers and Eukaryotic Expression* (1983)).

The vectors containing the gene encoding the protein of the invention are transformed into host cells for expression. The particular procedure used to introduce the genetic material into the host cell for expression of the protein is not particularly critical. Any of the well known procedures for introducing foreign nucleotide sequences into host cells can be used. It is only necessary that the particular procedure utilized be capable of successfully introducing at least one gene into the host cell which is capable of expressing the gene.

Transformation methods, which vary depending on the type of host cell, include electroporation; transfection employing calcium chloride, rubidium chloride calcium phosphate, DEAE-dextran, or other substances; microprojectile bombardment; lipofection; infection (where the vector is an infectious agent); and other methods (see generally Sambrook, supra, and *Current Protocols in Molecular Biology*, supra (Ausubel et al., eds., 1995). Reference to cells into which the nucleic acids described above have been introduced is meant to also include the progeny of such cells.

There are numerous prokaryotic expression systems known to one of ordinary skill in the art useful for the expression of the a recombinant protein. *E. coli* is commonly used, and other microbial hosts suitable for use include bacilli, such as *Bacillus subtilus*, and other enterobacteriaceae, such as Salmonella, Serratia, and various Pseudomonas species. Expression vectors for use in these prokaryotic hosts often contain a ribosomal binding site sequences for initiating and completing transcription and translation.

Host bacterial cells can be chosen that are mutated to be reduced in or free of proteases, so that the proteins produced are not degraded. For Bacillus expression systems, in which the proteins are secreted into the culture medium, strains are available that are deficient in secreted proteases.

Mammalian cell lines can also be used as host cells for the expression of the polypeptides used in the present invention. Propagation of mammalian cells in culture is per se well known (*Tissue Culture* (Kruse et al., eds. 1973)). Host cell lines may also include such organisms as yeast, filamentous fungi, plant cells, or insect cells, among others.

In one embodiment of antigen-APABP, as described in Example 1A, a nucleic acid was constructed that encodes a fusion protein, which contains amino acids 1–254 of LF and amino acids 1–511 of HIV envelope protein gp120. The nucleic acids were isolated using PCR and specific primers (SEQ ID NOS: 1–4) with restriction endonuclease sites at the ends. These sites were used to join the nucleic acids for LF and gp120. This recombinant nucleic acid construct was cloned into a GST expression vector, and protein was expressed and purified as described in Example 1A.

For the present invention, both *E. coli* and *B. anthracis* are examples of suitable expression systems. In one embodiment described in Example 1A, the LF-gp120 fusion protein was expressed and purified from *E. coli* according to standard methods.

c. Purification of Antigen Bound to Anthrax Protective Antigen Binding Protein

After protein expression using the recombinant nucleic acid-vector construct, the protein is then purified using standard techniques which are known in the art (see, e.g., Colley et al., *J. Biol. Chem.* 64: 17619–17622 (1989); and *Guide to Protein Purification*, in *Methods in Enzymology*, vol. 182 (Deutscher ed., 1990)).

If the expression system causes the protein of the invention to be secreted from the cells, the recombinant cells are grown and the protein is expressed, after which the culture medium is harvested for purification of the secreted protein. The medium is typically clarified by centrifugation or filtration to remove cells and cell debris and the proteins can be concentrated by adsorption to any suitable resin such as, for example, CDP-Sepharose, asialoprothrombin-Sepharose 4B, or Q Sepharose, or by use of ammonium sulfate fractionation, polyethylene glycol precipitation, or by ultrafiltration. Other means known in the art are equally suitable. Further purification of the protein can be accomplished by standard techniques, for example, affinity chromatography, ion exchange chromatography, sizing chromatography, or other protein purification techniques used to obtain homogeneity. The purified proteins are then used to produce pharmaceutical compositions, as described below.

Alternatively, vectors can be employed that express the protein intracellularly, rather than secreting the protein from the cells. In these cases, the cells are harvested, disrupted, and the protein is purified from the cellular extract, e.g., by standard methods. If the cell line has a cell wall, then initial extraction in a low salt buffer may allow the protein to pellet with the cell wall fraction. The protein can be eluted from the cell wall with high salt concentrations and dialyzed. If the cell line glycosolates the protein, then the purified glycoprotein may be enhanced by using a Con A column. Anion exchange columns (MonoQ, Pharmacia) and gel filtration columns may be used to further purify the protein. A highly purified preparation can be achieved at the expense of activity by denaturing preparative polyacrylamide gel electrophoresis.

Standard procedures that can be used further to purify proteins of the invention include ammonium sulfate precipitation, affinity and fraction column chromatography, and gel electrophoresis (see generally Scopes, *Protein Purification* (1982); U.S. Pat. No. 4,512,922 disclosing general methods for purifying protein from recombinantly engineered bacteria).

Recombinant proteins can be further concentrated by pressure dialysis and buffer exchanged directly into volatile buffers (e.g., N-ethylmorpholine (NEM), ammonium bicarbonate, ammonium acetate, and pyridine acetate). In addition, samples can be directly freeze-dried from such volatile buffers resulting in a stable protein powder devoid of salt and detergents. In addition, freeze-dried samples of recombinant analogs can be efficiently resolubilized before use in buffers compatible with infusion (e.g., phosphate buffered saline). Other suitable buffers might include hydrochloride, hydrobromide, sulphate acetate, benzoate, malate, citrate, glycine, glutamate, and aspartate.

In one embodiment of the invention, APABP-antigen protein was expressed intracellularly in *E. coli* and purified using glutathione S-transferase (GST) affinity, as described in Example 1A. In this example, the sequences encoding LF-gp120were ligated to sequences encoding GST in the expression vector pGEX-KG. After expression of the three-way fusion protein, a glutathione-Sepharose 4B column was used to rapidly purify the antigen-APABP (LF-gp120). The GST portion of the three-way fusion protein can then be removed by enzymatic cleavage at a specific site provided by a linker that is present in the three-way fusion protein. For use as a vaccine in humans, removal of the GST fusion region is the preferred embodiment.

d. Methods of Binding Antigen to APABP

As described above, antigen-APABP can be produced using recombinant nucleic acids that encode a single-chain fusion proteins. The fusion protein is expressed as a single chain using in vivo or in vitro biological systems.

Using current methods of chemical synthesis, antigen can be also be chemically bound to APABP for internalization into cells when administered with PA. The antigen-APABP can be tested empirically for internalization following the methods set forth in the Examples.

Functional groups capable of forming covalent bonds with the amino- and carboxyl-terminal amino acids or side groups of amino acids are well known to those of skill in the art. For example, functional groups capable of binding the terminal amino group include anhydrides, carbodiimides, acid chlorides, and activated esters. Similarly, functional groups capable of forming covalent linkages with the terminal carboxyl include amines and alcohols. Such functional groups can be used to bind antigen to APABP at either the amino- or carboxyl-terminus. Antigen can also be bound to APABP through interactions of amino acid residue side groups, such as the SH group of cysteine (see, e.g., Thorpe et al., *Monoclonal Antibody-Toxin Conjugates: Aiming the Magic Bullet*, in *Monoclonal Antibodies in Clinical Medicine*, pp. 168–190 (1982); Waldmann, *Science,* 252: 1657 (1991); U.S. Pat. Nos. 4,545,985 and 4,894,443) The procedure for attaching an agent to an antibody or other polypeptide targeting molecule will vary according to the chemical structure of the agent.

As example, a cysteine residue can added at the end of APABP. Since there are no other cysteines in LF, this single cysteine provides a convenient attachment point through which to chemically conjugate other proteins through disulfide bonds.

Although certain of the methods of the invention have been described as using LF fusion proteins, it will be understood that other LF compositions having chemically attached antigens can be used in the methods.

2. Protective Antigen a. Introduction

Wild type anthrax protective antigen (PA) combines with lethal factor (LF) to produce lethal toxin. In the present invention, PA binds to anthrax protective antigen binding protein, which is bound to an antigen (antigen-APABP). PA includes a cellular receptor binding domain, a translocation domain, and an LF binding domain. Each of these regions of the protein has an important role in the present invention. Protective antigen can be functionally described on the basis of three specific characteristics: its cellular binding activity, LF or antigen-APABP binding activity, and intracellular delivery of LF or antigen-APABP.

Cellular binding activity was demonstrated through structure-function and deletion analysis of wild type PA. PA binds specifically to a cell-surface receptor found on a wide variety of cell types (Leppla et al., in *Bacterial Protein Toxins*, pp. 111–112 (Fehrenbach et al., eds., 1988)). Structure-function experiments of protease-digested PA established that the carboxyl-terminus contains the receptor-binding domain (Novak et al., *J. Biol. Chem.,* 267: 17186–17193 (1992)). Further deletion analysis of the carboxyl-terminus revealed that mutant PA proteins truncated by 3, 5, or 7 amino acids at the carboxyl-terminus had a 2- to 10-fold reduction in cell binding activity (Singh et al., *J. Biol. Chem.,* 266: 15493–15497 (1991)). In addition, binding activity was lost upon deletion of 12 or 14 amino acids from the carboxyl-terminus (Singh, supra (1991)

The LF or antigen-APABP binding site of PA is revealed after formation of "processed" PA. After binding to the cell receptor, PA ("mature," 83 kDa) is enzymatically cleaved by a cellular protease (furin), which releases a 20 kDa amino-terminal fragment, leaving a 63 kDa "processed" carboxyl-terminal fragment bound to the cell receptor (Leppla et al., in *Molecular Mechanisms of Bacterial Virulence*, pp. 127–139 (Kado et al., eds, 1994)). The ability of PA to bind wild type LF or APABP-antigen was demonstrated with protease-digested PA. Limited in vitro trypsin digestion produced the biologically active 63 kDa AP processed fragment and the 20 kDa PA released fragment, while further digestion resulted in inactivation of biological activity. In addition, digestion of PA with chymotrypsin produced biologically inactive 37 and 47 kDa fragments (Novak, supra). Site-specific mutagenesis of the wild type PA cleavage site further demonstrated that cleavage is required for LF-binding activity (Singh et al., *J. Biol. Chem.*, 264: 19103–19107 (1989)).

PA is involved in internalization and delivery of LF or antigen-APABP to the cytosol. Conversion of PA to processed PA allows formation of an oligomeric form of PA that, after exposure to low pH in late endosomes, forms channels in cell membranes (Blaustein et al., *Proc. Natl. Acad. Sci. U.S.A.*, 86:2209–2213 (1989); Milne et al., *Mol. Microbiol.*, 10:647–653 (1993)). PA has also been shown to internalize fusion proteins composed of APABP bound to a second protein (Arora et al., *J. Biol. Chem.*, 267: 15542–15548 (1992); Arora et al., *Infect. Immun.*, 62: 4955–4961 (1994); Arora et al., *J. Biol. Chem.*, 69: 26165–26171 (1994)).

In the present invention, mature PA (83 kDa) is the preferred embodiment. PA processed in vitro by enzymes such as trypsin, furin, and clostripain can be used in the present invention. Stability of in vitro processed PA is enhanced by the presence of LF or APAPB. In addition to full length recombinant PA, amino-terminal deletions up to the 63 kDa cleavage site or additions to the full length PA are useful. A recombinant form of processed PA is also biologically active and could be used in the present invention. Although the foregoing describes specific deletion and structure-function analysis of PA, any biologically active form of PA can be used in the present invention.

b. Cloning and Expression of a Nucleic Acid Encoding Protective Antigen

In general, for cloning and expression of PA, the same methods as described for antigen-APABP can be used by one skilled in the art. Genes that encode wild type or mutated proteins can be cloned and expressed by methods known to those skilled in the art, as described above. For example, the gene encoding protein Ib of the *Clostridium perfringens* iota toxin can be cloned and expressed for use in the present invention according the methods described herein, or by methods known to those skilled in the art. The present invention uses an isolated nucleic acid in expression vector pYS5 that encodes the PA protein, as described in Example 2.

3. In vitro Testing for MHC Class I Presentation and Antigen Recognition by Cytotoxic T Lymphocytes The ability of antigen-APABP and PA to deliver antigens for processing and presentation via the MHC class I pathway can be tested in vitro. Cells that present the processed antigen with MHC class I molecules are recognized and killed by specific cytotoxic T cells.

In a typical cytotoxic T lymphocyte assay (CTL assay), antigen-APABP and PA are administered to a target antigen-presenting cell. Any suitable cell line can be used for presentation of antigen, since MHC class I molecules are present in most cell types (see, e.g., Watson et al., *Molecular Biology of the Gene*, pp. 880–881 (4th ed. 1987). The CTLs used in the assay require two specific characteristics. First, the CTLs must have been conditioned to recognize the specific antigen in antigen-APABP. This specificity can be attained by culturing T cells from a previously immunized mammal. The specificity of the CTL response can be increased by stimulating and cloning the T cells in vitro. Second, the CTLS must come from the same genetic background as the antigen-presenting cells so that they specifically recognize the antigen displayed with the MHC class I molecule as foreign.

To demonstrate that the antigen from antigen-APABP is properly presented and recognized by CTL, target antigen-presenting cells and effector CTL cells are mixed in culture and target cell lysis is observed. Any suitable method for measuring cell lysis can be used by one skilled in the art. For example, a radioactivity release assay can be used to measure lysis of the target cells. After target cells are treated with PA and antigen-APABP for a suitable time, the target cells are labeled with radioactive reagents such as $^{51}$Cr, which are taken up by live cells. Following labeling, the target cells are washed and mixed with specific CTLs. Supernatants are harvested after a suitable time and counted to determine the percent radioactivity release. Other methods to determine the amount of cell lysis include trypan blue exclusion, in which living cells that exclude the dye are counted and compared to a control sample of non-presenting cells treated in the same manner.

Example 3 describes one embodiment of this test. The example uses mouse mastocytoma cells as the antigen-presenting cells, CTL line 9.23.3, which recognizes a specific gp120 epitope, and a $^{51}$Cr release assay for cell lysis.

To confirm the dependence of antigen-APABP on processing by the classical MHC class I pathway, the ability of the specific proteasome inhibitor, lactacystin, to inhibit presentation of the antigen can be tested. Incubation of mouse mastocytoma cells with 10 $\mu$M lactacystin for 45 minutes prior to the addition of PA and LF-gp120 (from Example 1A) significantly decreased lysis of the target cells by CTLs. Lactacystin inhibition of peptide presentation shows that the processing of the peptide epitope from the fusion protein depends on the function of the proteasome complex. This dependence precludes the role of any alternate processing pathways for presentation by the anthrax toxin LF-gp120 fusion protein.

4. In vivo Testing of Mice and Other Mammals for MHC class I Presentation and Antigen Recognition by the Cell-mediated Immune System Mammals can be tested for MHC class I presentation of antigen-APABP. Standard procedures known to those skilled in the art can be used to immunize mice, cats, and other mammals including humans. The PA/antigen-APABP composition can be administered in any suitable method, for example, parenterally. In some examples, animals can receive additional injections of the PA/antigen-APABP composition.

Subject mammals can be tested for an immune response to the administered antigen in any suitable manner. For example, animals can be challenged with the antigen after immunization. The effectiveness of immunization can be measured after antigen challenge by observing if the animals develop symptoms of the disease. Animals can also be tested for disease-indicating markers, such as toxins or viral enzymes. Subject animals can also be tested for a specific cellular-based immune response using a CTL assay, as described above.

In one embodiment of the invention (described in Example 4), a composition of PA and LF-gp120 was administered to mice. The mice received a single injection of the PA/LF-gp120 composition in 100 $\mu$l of PBS, either subcutaneously or intraperitonealy. The mice injected with the PA/LF-gp120 composition were sacrificed after three weeks, and their spleens were harvested for collection of CTLs. The CTLs were restimulated in vitro with a small peptide epitope from gp120 to expand the specific CTL population that recognizes the antigen. The CTLs were then mixed with antigen-presenting cells (mouse mastocytoma cells treated with PA/LF-gp120 as described above and in Example 3). Lysis of the antigen-presenting cells by the CTL population is measure by standard methods, for example, with the $^{51}$Cr release assay described above and in Example 3.

5. How to Make a Vaccine Using the Present Invention

Depending on the intended mode of administration, the compounds of the present invention can be in various pharmaceutical compositions. The compositions will include a unit dose of the selected proteins, including antigen-APABP and PA, in combination with a pharmaceutically acceptable carrier and, in addition, can include other medicinal agents, pharmaceutical agents, carriers, adjuvants, diluents, and excipients. The ratio of PA to antigen-APABP is greater than 1 by molar excess, and preferably 2–4. "Pharmaceutically acceptable" means a material that is not biologically or otherwise undesirable, i.e., the material can be administered to an individual along with the fusion protein or other composition without causing any undesirable biological effects or interacting in a deleterious manner with any of the other components of the pharma-ceutical composition in which it is contained.

Examples of physiologically acceptable carriers include saline solutions such as normal saline, Ringer's solution, PBS (phosphate-buffered saline), and generally mixtures of various salts including potassium and phosphate salts with or without sugar additives such as glucose. Suitable excipients are, for example, water, saline, dextrose, glycerol, and ethanol. Nontoxic auxiliary substances, such as wetting agents, buffers, or emulsifiers may also be added to the composition. In one embodiment of the invention, adjuvants are not required for immunization.

Parenteral administration, if used, is generally characterized by injection. Sterile injectables can be prepared in conventional forms, either as liquid solutions or suspensions, solid forms suitable for solution or suspension in liquid prior to injection, or as emulsions.

6. How to Administer the Vaccine Using the Present Invention

For each recipient, the total vaccine amount necessary can be deduced from protocols for immunization with other vaccines. The exact amount of such antigen-APABP and PA compositions required will vary from subject to subject, depending on the species, age, weight and general condition of the subject, the particular fusion protein used, its mode of administration, and the like. Generally, dosage will approximate that which is typical for the administration of other vaccines, and will preferably be in the range of about 10 ng/kg to 1 mg/kg.

The recipient is a mammal, e.g., a cat, dog, horse, cow, pig, sheep, goat, or human. Although human use is preferred, veterinary use of the invention is also feasible. For example, cats suffer from a so-called feline AIDS or feline immunodeficiency virus (FIV). Antigen-APABP and PA can be administered as a vaccine to produce an immune response in cats to FIV.

The vaccine is administered as a sterile composition. The fusion proteins and other compositions of the invention can be administered by any suitable means, e.g., parenterally (subcutaneously, intramuscularly, or intraperitoneally), intravenously, or orally. Preferably, the proteins are administered parenterally, with subcutaneous administration being the most preferred route because it provides the composition to dendritic cells, which have strong antigen-presenting characteristics. An appropriate evaluation of the time and method for delivery of the vaccine is well within the skill of the clinician.

The timing of administration of the vaccine and the number of doses required for immunization can be determined from standard vaccine administration protocols. Typically, as described in Example 5, in one embodiment, a vaccine composition will be administered in two doses. The first dose will be administered at the elected date and a second dose will follow at one month from the first dose. A third dose may be administered is necessary, and desired time intervals for delivery of multiple doses of a particular antigen-APABP can be determined by one of ordinary skill in the art employing no more than routine experimentation (see, e.g., Product Information, *Physician's Desk Reference* (1996)).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1A

Construction and Expression of an Anthrax Lethal Factor/HIV gp120 Fusion Protein Restriction endonucleases and DNA modifying enzymes were purchased from Life Technologies, Boehringer Mannheim, or New England BioLabs. Oligonucleotides were synthesized using an automated nucleic acid synthesizer (Applied Biosystems) and purified on oligonucleotide purification cartridges (Applied Biosystems). Polymerase chain reaction (PCR) was performed with a GeneAmp kit according to the manufacturer's directions (Perkin-Elmer Cetus). Bacterial media preparation, restriction digests, ligation, and phosphatase treatment of DNA were performed by standard protocols (Sambrook, supra).

a. Antigen-APABP Plasmid Construction

Construction of the plasmid used to express the LF-gp120 fusion protein in *E. coli* was performed as follows. The pGEX-KG vector (Pharmacia), which contains a glutathione S-transferase protein coding region, was ligated with PCR-amplified LF and gp120 gene sequences to produce a plasmid encoding a three-way fusion protein. The fusion protein contains the 26 kDa GST region, a 14 amino acid linker, amino acids 1–254 of LF, and amino acids 1–511 of gp120.

The DNA encoding amino acids 1–254 of LF was amplified from plasmid pLF7 with primers that added unique XbaI and MluI sites on the 5' and 3' ends, respectively (Robertson & Leppla, *Gene* 44: 71–78 (1986)). The sequences of the primers were:

5'-TCTAGATCTAGAAGCGGGCGGTCATGGT
GATGTAGG-3' (primer 1, SEQ ID NO: 1)

and

5'-GATCTTTAAGTTCACGCGTGGATAGATTT
ATTTCTTG-3' (primer 2, SEQ ID NO: 2).

The DNA encoding amino acids 1–511 of gp120 was amplified from plasmid HXB2-env with primers that added unique sites for MluI and PstI on the 5' end and unique XbaI and XhoI sites on the 3' end of the amplified gene (Page et al., *J Virol.* 64: 5270–5276 (1990)). The sequences of the primers were:

5'-GCAAGACGCGTCTGCAGATGAGAGTG
AAGGAG-3' (primer 3, SEQ ID NO: 3)

and

5'-ATCCGCTCGAGTCTAGATTATCTTTTTCT
CTCTGCAC-3' (primer 4, SEQ ID NO:,4).

Primer 4 introduced a stop sequence (TAA) after the gp120 coding sequence.

The amplified DNA products and the pGEX-KG plasmid DNA were digested with the appropriate restriction enzymes. Vector DNA was dephosphorylated with bacterial alkaline phosphatase for 30 minutes. All three DNA fragments were purified from low melting point agarose after electrophoresis by extraction with phenol-chloroform, mixed and ligated overnight at 16° C. with T4 DNA ligase.

The ligated DNA was used to transform chemically competent *E. coli* (DH5α, high efficiency, Life Technologies). Transformed *E. coli* were selected on ampicillin-containing solid media (50 μg/ml) and screened by restriction analysis of extracted plasmid. Clones that had the expected restriction pattern were confirmed by DNA sequencing.

The resulting recombinant nucleic acid in the pGEX-KG vector was referred to as the LF-gp120 fusion protein construct. The carboxy-terminal residue of the linker from pGEX-KG was changed from D to E and four residues, TRLQ, were added between the LF and gp120 portions of the construct due to DNA manipulations. The LF-gp120 recombinant nucleic acid encodes a fusion protein that has a calculated molecular weight of 114,852 daltons and a calculated pI of 7.00.

b. Expression and Purification of the LF-gp120 Fusion Protein

The LF-gp120 fusion protein construct was used to express the three-part fusion protein (GST-LF-gp120). Glutathione S-transferase (GST) typically imparts greater solubility to the expressed fusion protein and enables purification of the fusion protein on glutathione affinity columns. The GST region can be removed from the fusion protein by digestion with a site-specific protease that recognizes a linker region in the fusion protein. In this Example the GST region was not removed, however, removal is preferred for use as a human vaccine. The expression and purification of GST-LF fusion proteins was described previously (Arora & Leppla, *Infect. Immun.* 62: 4955–4961 (1994)). Expression and purification of the LF-gp120fusion protein in *E. coli* was performed as follows. *E. coli* strain SG12036 was transformed with the recombinant LF-gp120fusion protein construct and grown in rich media (superbroth, 100 μg/ml of ampicillin) with shaking at 225 rpm at 37° C. When the cell density at $A_{600}$ reached 0.6–0.8, expression of the fusion protein was induced by adding iso-propyl-1-thio-b-D-galactopyranoside (IPTG) to a final concentration of 1 mM.

After further incubation for 2 hours, the bacterial cells were pelleted by centrifugation and then resuspended in 100 mM phosphate buffer (pH 7.4), 150 mM NaCl, 1% Triton X-100, 5 mM EDTA, 5 μg/ml leupeptin, 10 μg/ml aprotinin, and 10 μg/ml 4-(2-aminoethyl)-benzenesulfonylfluoride. The bacterial cells were disrupted by sonication and the clarified extracts applied to a glutathione-Sepharose 4B column previously equilibrated with buffer (100 mM phosphate (pH 7.4), 150 mM NaCl, 1% Triton X-100). The column was washed extensively and the bound fusion protein was eluted with 10 mM glutathione in 50 mM Tris (pH 8.0), 0.5 mM EDTA.

The eluted protein was concentrated by ultrafiltration with a Centriprep-30 device (Amicon) and analyzed for purity by electrophoresis on nondenaturing- and SDS-polyacrylamide gels (Phast gels, Pharmacia). Protein concentrations were determined by the micro BCA method with bovine serum albumin as a standard (Pierce).

Example 1B

Construction and Expression of an Hepatitis C NS-5b/anthrax Lethal Factor Fusion Protein A recombinant plasmid encoding a LF-NS-5b fusion protein is constructed using the methods described in Example 1a, substituting DNA sequences encoding the hepatitis C protein NS-5b for the DNA sequences encoding gp120.

Example 2

Protective Antigen Plasmid Construction and Protein Expression and Purification

Protective antigen was expressed in *B. anthracis* from the expression vector pYS5 and purified by established procedures (Singh et al., *J. Biol. Chem.* 264: 19103–19107 (1989); Leppla, in *Methods in Enzymology*, vol. 165, pp. 103–116 (Harshman ed., 1988). Mutant PA molecules PA CFD and PA--D were constructed by site-directed mutagenesis and have been previously described (Singh et al., *J. Biol. Chem.* 269: 29039–29046 (1994)). The mutant PA molecules were used as negative controls in Example 3.

Example 3

In vitro Presentation of LF-gp120 Antigen by Mouse Mastocytoma Cells and Lysis with a gp120 Effector Cytotoxic T Lymphocyte Cell Line The LF-gp120 fusion protein and PA were tested in vitro for their ability to deliver antigenic proteins to the cell cytosol for processing and presentation with MHC class I molecules on the cell surface. Mouse mastocytoma cells were used as the target antigen-presenting cell. Cytotoxic T lymphocytes that recognized the peptide epitope RGPGRAFVTI (SEQ ID NO:5) from the V3 loop of gp120 were used with a $^{51}$Cr-release assay to examine specific lysis of the antigen presenting target cell population. Translocation-deficient mutant PA proteins or the absence of PA were used as controls to demonstrate that processing of the fusion protein relies on internalization via the PA receptor.

a. Cell Lines

The following cell lines were used in this example. P815, a DBA/2 derived ($H-2^d$) mastocytoma (ATCC TIB-64) was used as target cells in the cytotoxic T lymphocyte (CTL) assay. These cells were maintained in RPMI1640 supplemented with 10% FCS. The HIV gp120-specific CTL line 9.23.3 that recognizes the V3 epitope RGPGRAFVTI (SEQ ID NO:5) that has been previously described (Takahashi et al., *Proc. Natl. Acad. Sci. U.S.A.* 85: 3105–3109 (1988); Alexander-Miller et al., *Proc. Natl. Acad. Sci. U.S.A.* 93: 4102–4107 (1996); Shirai et al., *J Immunol.* 148: 1657–1667 (1992)). Peptide P18IIIB that recognizes this epitope was made by an automated peptide synthesizer (Applied Biosystems) and purified by high performance liquid chromatography before use. The HIV gp120-specific CTL line was derived from BALB/C spleens taken from mice previously immunized with a recombinant vaccinia virus expressing the gp120 protein. 9.23.3 CTL were stimulated with 10 $\mu$m free P18IIIB peptide at $5\times10^5$ CTL, and $5\times10^6$ irradiated spleenocytes [3000 rads (1 rad=0.01 Gy)] per well, in a 24-well plate containing 2 ml of a 1:1 mixture of RPMI1640 medium and Eagle-Hank's amino acid medium (EHAA) supplemented with L-glutamine, sodium pyruvate, nonessential amino acids, penicillin, streptomycin, $5\times10^5$ M 2-mercaptoethanol, 10% fetal calf serum, and 10% T-stim (Collaborative Biomedical Products).

b. $^{51}$Cr Release Assay Method

The following assay method was used to measure target cell lysis by CTLs. $^{51}$Cr release assays were performed as previously described (Alexander et al., *J. Exp. Med.* 173: 849–858 (1991)). When appropriate, target cells were treated with PA (100 ng/ml) and/or LF-gp120 fusion protein (50 ng/ml when used with 9.23.3 CTL) for 12 hours in serum-free media. After treatment the target cells ($5\times10^5$ cells) were labeled with 200 $\mu$Ci (1 Ci=37 Gbq) of $Na_2{}^{51}CrO_4$ in 100 $\mu$l of RPMI1640 for 2 hours at 37° C. In some cases, target cells were pulsed with peptide (1.0–10.0 $\mu$M) during labeling. Following labeling, targets were washed 3 times and added at 3000 cells/well along with the appropriate number of effector cells in 96-well round-bottom plates. Supernatants were harvested after 6 hours and counted in an ISOMEDIC gamma counter (ICN, Horsham, Pa.). The mean of triplicate samples was calculated and the percent $^{51}$Cr release determined using the following formula. Percent $^{51}$Cr release=100× [(experimental $^{51}$Cr release−control $^{51}$Cr release)/(maximum $^{51}$Cr release−control $^{51}$Cr release)], where experimental $^{51}$Cr release represents counts from target cells mixed with effector cells, control $^{51}$Cr release represents target cells mixed with medium alone (spontaneous release), and maximum $^{51}$Cr release represents counts from target cells exposed to 2.5% Triton X-100.

c. Specific Cytolysis of Target Cells Sensitized with LF-gp120 Fusion Proteins by HIV gp120 Specific CTL In order to measure gp120 antigen presentation via processing of LF-gp120 in the MHC class I processing pathway, the mouse mastocytoma cell line P815 was incubated with PA or PA mutants and/or LF-gp120 fusion protein for 12 hours under serum-free conditions. The cells were then washed and labeled with $^{51}$Cr for use as target cells. The labeled P815 target cells were mixed at different ratios with the effector CTL cell line 9.23.3. Killing of the target cell population was determined by measuring release of $^{51}$Cr into the media.

Target cells treated with wild type PA and LF-gp120 fusion protein were efficiently recognized and lysed by the 9.23.3 CTL line. The recognition and lysis was dependent on the presence of functional PA, demonstrating that processing and presentation of the fusion protein relies on internalization via the PA receptor.

Treatment with a translocation-defective mutant PA protein (Singh et al., *J. Biol. Chem.* 269: 29039–29046 1994)), or without the addition of PA resulted in minimal lysis of the target cells. This result demonstrates that a limited amount of LF-gp120 is proteolytically degraded extracellularly, sensitizing target cells without active transport into the cytosol. This result implies that the LF-gp120 fusion protein needs to gain access to the cell cytosol for efficient processing and presentation via the MHC class I processing pathway. Treatment with PA alone, mutant PA alone, or the LF-gp120 fusion alone did not sensitize the target cells for lysis. As a positive control, the peptide P18IIIB was added to the external medium of the target cells. Incubation of the target cells in the presence of P18IIIB did result in cell lysis when effector cells were added.

Example 4

In vivo Immune Response to LF-gp120 Fusion Protein in Mice

Mice were tested in vivo for MHC class I presentation of gp120 and stimulation of specific CTL using the LF-gp120 fusion protein. LF-gp120 and PA were administered to mice in a single injection of the composition in 100 $\mu$l of PBS, both subcutaneously and intraperitonealy.

Subject animals were tested for a specific cell-mediated immune response using a CTL assay, as described in Example 3. Mice injected with the PA/LF-gp120 composition were sacrificed after three weeks, and their spleens were harvested for collection of CTLs. The CTLs were restimulated in vitro with a small peptide described in Example 3 that recognizes a gp120 epitope. The CTLs were then mixed with antigen-presenting cells (mouse mastocytoma cells treated with LF-gp120 and PA as described in Example 3). lysis of the antigen-presenting cells by the CTL population was measured by $^{51}$Cr release assay, as described above. Mice injected with the PA/LF-gp120 composition demonstrated a strong CTL response to gp120 presenting cells.

Example 5

In vivo Immune Response to LF-gp120 Fusion Protein in Humans

A human subject who is HIV negative will be tested for an immune response to a sterile vaccine formulation of the LF-gp120 fusion protein. The sterile vaccine formulation will be composed of a unit dose of LF-gp120 with a 2–4 molar excess of PA in PBS. A typical unit dose will be 10 ng of LF-gp120 fusion protein per kilogram of the human subject. The vaccine formulation will be administered subcutaneously in two doses. The first dose will be at the elected date and a second dose will follow at one month from the first dose.

The immune response to the administered vaccine will be measured by testing the subject for gp120 antibody production. Blood will be taken at on a standard schedule according to standard procedures from the subjects who received the vaccine, and antibodies to gp120 will be measured with standard ELISA and western blot techniques.

As a more specific test of cellular immune response, a skin test or purified protein derivative (PPD) test will be used. A unit dose of the PA/LF-gp120 composition in PBS will be injected under the skin of the previously immunized human subject, according to standard procedures. The area will be examined at 48–72 hours for redness and swelling, which indicates a cellular immune response based on previous exposure to the antigen (see *Harrison's Principles of Internal Medicine* (Isselbacher et al., eds., 13th ed. 1994).

What is claimed is:

1. A method of immunizing a mammal against cytotoxic T cell epitopes of a specific full length protein antigen, the method comprising the step of administering a safe and effective amount of a binary, cytotoxic T lymphocyte vaccine comprising an anthrax protective antigen and the full length protein antigen bound to a nontoxic anthrax protective antigen binding protein comprising at least about the first 250 amino acid residues of the lethal factor of *Bacillus anthracis* and less than all of the amino acid residues of the lethal factor, wherein the full length protein antigen is processed into multiple epitopes in a cytosolic MHC class I processing pathway and presented by MHC class I molecules to cytotoxic T lymphocytes.

2. The method of claim 1 wherein the protective antigen is a processed protective antigen.

3. The method of claim 1 wherein the vaccine is sterile.

4. The method of claim 1 wherein the vaccine further comprises physiologically compatible salts.

5. The method of claim 4 wherein the vaccine is in an aqueous solution of physiologically compatible salts.

6. The method of claim 1 wherein the molar ratio of protective antigen to the antigen bound to an anthrax protective antigen binding protein is greater than one.

7. The method of claim 1 wherein the vaccine is administered via parenteral injection.

8. The method of claim 1 wherein the vaccine is administered via subcutaneous injection.

9. The method of claim 1 wherein the vaccine is administered in a unit dose that is between 10 to 500 nanograms of antigen bound to an anthrax protective antigen binding protein per kilogram of said mammal.

10. The method of claim 1, wherein the anthrax protective antigen binding protein is amino acids 1–254 of lethal factor.

* * * * *